US012583811B2

(12) United States Patent
Lee et al.

(10) Patent No.: US 12,583,811 B2
(45) Date of Patent: Mar. 24, 2026

(54) METHOD FOR PREPARING LINEAR HYDROCARBON DOUBLE ACID WITH CYCLIC HYDROCARBON OXIDATION CATALYST

(71) Applicants: KOREA ADVANCED INSTITUTE OF SCIENCE AND TECHNOLOGY, Daejeon (KR); HANWHA SOLUTIONS CORPORATION, Seoul (KR)

(72) Inventors: Jae Woo Lee, Daejeon (KR); Jeil Park, Daejeon (KR); Wonhyeong Lee, Daejeon (KR)

(73) Assignees: KOREA ADVANCED INSTITUTE OF SCIENCE AND TECHNOLOGY, Daejeon (KR); HANWHA SOLUTIONS CORPORATION, Seoul (KR)

( * ) Notice: Subject to any disclaimer, the term of this patent is extended or adjusted under 35 U.S.C. 154(b) by 460 days.

(21) Appl. No.: 18/251,015

(22) PCT Filed: Oct. 28, 2021

(86) PCT No.: PCT/KR2021/015305
§ 371 (c)(1),
(2) Date: Apr. 28, 2023

(87) PCT Pub. No.: WO2022/092851
PCT Pub. Date: May 5, 2022

(65) Prior Publication Data
US 2024/0343668 A1 Oct. 17, 2024

(30) Foreign Application Priority Data
Oct. 30, 2020 (KR) ........................ 10-2020-0143258

(51) Int. Cl.
*C07C 51/31* (2006.01)
*B01J 23/34* (2006.01)
(Continued)

(52) U.S. Cl.
CPC ............. *C07C 51/313* (2013.01); *B01J 23/34* (2013.01); *B01J 23/75* (2013.01); *B01J 23/8892* (2013.01);
(Continued)

(58) Field of Classification Search
CPC ....... C07C 51/313; C07C 51/31; C07C 55/14; C07C 55/21; C07C 44/14; C07C 44/21; B01J 23/8892; B01J 27/198; B01J 23/75
See application file for complete search history.

(56) References Cited

FOREIGN PATENT DOCUMENTS

| | | | | |
|---|---|---|---|---|
| CN | 102755907 A | | 10/2012 | |
| EP | 1325901 | * | 7/2003 | ............. C07C 51/03 |

(Continued)

OTHER PUBLICATIONS

Alshehri, A.A., et al., New catalysts with dual-functionality for cyclohexane selective oxidation, Applied Catalysis A, General, vol. 554, pp. 71-79 (Year: 2018).*

(Continued)

*Primary Examiner* — Yate' K Cutliff
(74) *Attorney, Agent, or Firm* — Harvest IP Law, LLP

(57) ABSTRACT

The present invention relates to a method for preparing hydrocarbon double acids using a cyclic hydrocarbon oxidation catalyst, wherein adipic acid and dodecanedioic acid may be produced with high yield while solving the problem of environmental pollution, the adipic acid and the dodecanedioic acid being prepared by using an oxidation reaction of a cyclohexane-cyclohexanone mixture and an oxidation reaction of a cyclododecane-cyclododecanone mixture,
(Continued)

respectively, in the presence of a vanadium phosphate oxide-based catalyst and/or a cobalt-manganese oxide-based catalyst.

15 Claims, 3 Drawing Sheets

(51) Int. Cl.

| | |
|---|---|
| ***B01J 23/75*** | (2006.01) |
| ***B01J 23/889*** | (2006.01) |
| ***B01J 27/198*** | (2006.01) |
| ***C07C 55/14*** | (2006.01) |
| ***C07C 55/21*** | (2006.01) |

(52) U.S. Cl.

CPC ............ *B01J 27/198* (2013.01); *C07C 51/31* (2013.01); *C07C 55/14* (2013.01); *C07C 55/21* (2013.01); *B01J 2235/05* (2024.01); *B01J 2235/15* (2024.01); *C07C 2601/14* (2017.05)

(56) References Cited

FOREIGN PATENT DOCUMENTS

| | | | |
|---|---|---|---|
| EP | 1 350 786 | B1 | 8/2008 |
| EP | 1325901 | A1 | 7/2023 |
| JP | 2002030027 | A | 1/2002 |
| KR | 2002030027 | A | 1/2002 |
| WO | 01/87815 | A2 | 11/2001 |

OTHER PUBLICATIONS

Jian, J., et al., Boosting one-step conversion of cyclohexane to adipic acid by NO2 and VPO composite catalyst, ChemComm, Royal Society of Chemistry, vol. 52, No. 16, pp. 1-5 (Year: 2016).*

Alshehri Amal A.; Alhanash Abdullah M.; Eissa Murad; Hamdy Mohamed S.: "New catalysts with dual-functionality for cyclohexane selective oxidation", Applied Catalysis A: General, Elsevier, Amsterdam, NL, vol. 554, Jan. 31, 2018 (Jan. 31, 2018), pp. 71-79, XP085352484.

Jian Jian, You Kuiyi, Duan Xuezhi, Gao Hongxu, Luo Qing, Deng Renjie, Liu Pingle, Ai Qiuhong, Luo He'an: "Boosting one-step conversion of cyclohexane to adipic acid by NO 2 and VPO composite catalysts", Chemical Communications, Royal Society of Chemistry, UK, vol. 52, No. 16, Feb. 25, 2016 (Feb. 25, 2016), pp. 3320-3323, XP055927387.

Alberto Mazzi et al: "Cyclohexane Oxidation to Adipic Acid Under Green Conditions: A Scalable and Sustainable Process", Chemcatchem, John Wiley & Sons, Inc, Hoboken, USA, vol. 10, No. 17, Jun. 28, 2018 (Jun. 28, 2018), pp. 3680-3682, XP072431955.

European Search Report for a corresponding EP patent application, Oct. 23, 2024.

Office Action from Korean Patent Office Dated Jan. 21, 2025 Issued for Korean Patent Application 10-2020-0143258.

Cyclohexane oxidation to adipic acid under green conditions: a scalable and sustainable process. A. Mazzi et al. (2018) Wiley-VCH, ChemCatChem Cataysis 10.1002/cctc.201800419 See Abstract.

New catalysts with dual-functionality for cyclohexane selective oxidation, Amal A. Alshehria et al. Applied Catalysis A, General 554 (2018) 71-79, See Abstract.

Relationship between bulk phase, near surface and outermost atomic layer of VPO catalysts and their catalytic performance in the oxidative dehydrogenation of ethane, Francisco Ivars-Barcel et al. Journal of Catalysis 354 (2017) 236-249, See Abstract.

Boosting one-step conversion of cyclohexane to adipic acid by NO2 and VPO composite catalysts, Jian Jian et al. The Royal Society of Chemistry (Jan. 21, 2016) DOI: 10.1039/b000000x, See Abstract.

Synergistic effect of co-reactant promotes one-step oxidation of cyclohexane into adipic acid catalyzed by manganese porphyrins, Hui Li et al. Can. J. Chem. (2015), See Abstract.

An effective Mn—Co mixed oxide catalyst for the solvent-free selectiveoxidation of cyclohexane with molecular oxygen, Mingzhou Wu et al. Applied Catalysis A: General 523 (2016) 97-106, See Abstract.

Oxidation of Cyclohexane, Cyclohexanone, and Cyclohexanol to Adipic Acid by a Non-HNO3 Route over Co/Mn Cluster Complexes, National Chemical Laboratory, Pune 411 008, India (Jul. 25, 2002) 39-45, See Abstract.

Office Action from Japanese Patent Office Dated Apr. 30, 2024, Issued for Japanese Patent Application No. 2023-526331.

* cited by examiner

METHOD FOR PREPARING LINEAR HYDROCARBON DOUBLE ACID WITH CYCLIC HYDROCARBON OXIDATION CATALYST

CROSS-REFERENCE TO RELATED APPLICATION(S)

This application is a National Stage of International Application No. PCT/KR2021/015305 filed Oct. 28, 2021, claiming priority based on Korean Patent Application No. 10-2020-0143258 filed Oct. 30, 2020, the disclosure of which is incorporated herein by reference in its entirety.

TECHNICAL FIELD

The present invention relates to a method for preparing a linear hydrocarbon double acid using a cyclic hydrocarbon oxidation catalyst, and in particular, to a method for producing linear hydrocarbon double acids such as adipic acid and dodecanedioic acid with high yield without producing nitrous oxide by oxidizing a cyclic hydrocarbon compound of a C6 to C12 cycloalkane and/or C6 to C12 cycloketone in the presence of a vanadium phosphate oxide-based catalyst and/or a cobalt-manganese oxide-based catalyst.

BACKGROUND ART

Adipic acid, which is a dicarboxylic acid composed of six carbons, is a raw material of nylon-6,6 polyamide, and its production method has been steadily developed and improved since commercial production began in the 1930s by Du Pont. Currently, cyclohexane is used as a reactant in a reaction that commercially produces adipic acid. When cyclohexane is primarily oxidized using oxygen, a mixture of cyclohexanol and cyclohexanone is obtained, and when the mixture is further oxidized using nitric acid, adipic acid is finally obtained. However, in this case, nitrous oxide is also produced as a by-product, which is a greenhouse gas that rises to the stratosphere and destroys the ozone layer when emitted as it is. Therefore, an additional process for separating nitrous oxide is required, which becomes a factor that reduces the economic feasibility of producing adipic acid. In addition, in order to produce adipic acid from cyclohexane, the ring structure of cyclohexane should be broken. Since cyclohexane is a stable substance, oxidation does not proceed to adipic acid in many cases, and thus a cyclohexane conversion and an adipic acid selectivity decrease.

Dodecanedioic acid is a dicarboxylic acid composed of 12 carbons and is used as a core raw material for polymer products such as polyamide, polyester, and polyurethane. Preparation of dodecanedioic acid is largely divided into chemical preparation using cyclododecane as a reactant and biological preparation using biowaste. In this case, in the chemical preparation method, nitric acid is also used for the oxidation of cyclododecanone, which is an intermediate.

Therefore, many studies on a method for oxidizing a cyclic hydrocarbon without using nitric acid as an oxidizing agent have been conducted. A. Mazzi et al. oxidized cyclohexane using a vanadium phosphorus oxide (VPO) catalyst supported on a cerium oxide support and showed that the reactivity varied depending on a catalyst support (A. Mazzi, S. Paul, F. Cavani, and R. Wojcieszak, ChemCatChem, 10:3680-3682 (2018)), but did not mention the type of synthesized VPO catalyst phase or its effect. F. Ivars-Barceló et al. described that a selectivity of a product varies when the oxidation number of vanadium changes due to a change in VPO phase, and suggested a method for synthesizing several types of VPO phases (F. Ivars-Barceló, G. J. Hutchings, J. K. Bartley, S. H. Taylor, P. Sutter, . . . and B. Solsona, Journal of catalysis, 354:236-249 (2017)). In addition, M. Wu et al. oxidized cyclohexane using a Mn—Co catalyst, but the catalyst was not supported on a support and the yield of adipic acid produced was significantly low (M. Wu, W. Zhan, Y. Guo, Y. Guo, Y. Wang, L. Wang, and G. Lu, Applied Catalysis A: General, 523:97-106 (2016)).

Accordingly, as a result of intensive efforts to solve the above problems, the present inventors have confirmed that linear hydrocarbon double acids such as adipic acid and dodecanedioic acid may be produced with high yield without producing nitrous oxide, which is a greenhouse gas, when a cyclic hydrocarbon compound of a C6 to C12 cycloalkane and/or C6 to C12 cycloketone is oxidized in the presence of a vanadium phosphate oxide (VPO)-based catalyst or a cobalt-manganese oxide-based catalyst supported on a mesoporous silica support, thereby completing the present invention.

SUMMARY OF INVENTION

An object of the present invention is to provide a method for producing linear hydrocarbon double acids such as adipic acid and dodecanedioic acid with high yield without producing nitrous oxide, which is a greenhouse gas.

In order to achieve the above object, the present invention provides a method for preparing hydrocarbon double acids, the method including oxidizing one or more cyclic hydrocarbon compounds selected from the group consisting of C6 to C12 cycloalkanes and C6 to C12 cycloketones in the presence of a vanadium phosphate oxide-based catalyst, a cobalt-manganese oxide-based catalyst, or a mixture thereof.

DETAILED DESCRIPTION OF INVENTION AND SPECIFIC EMBODIMENTS

Figure 1:
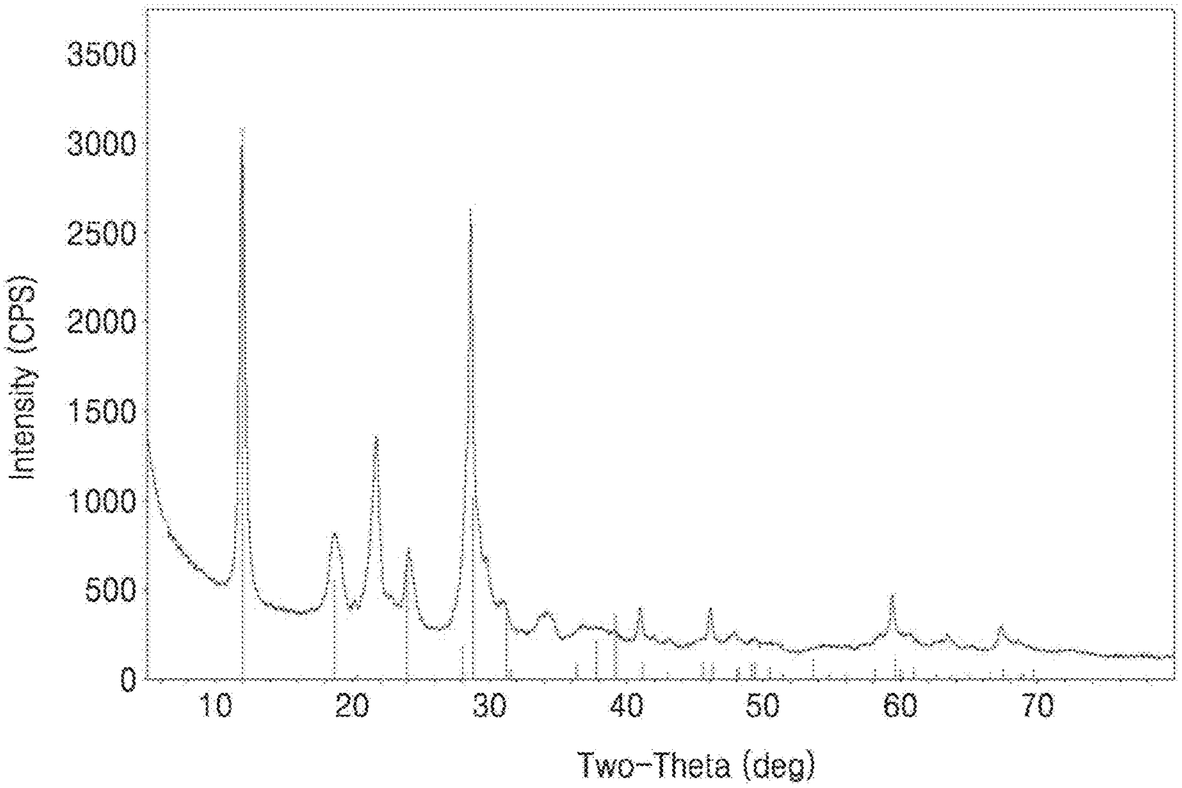
FIG. 1 is a graph showing a schematic form of XRD peaks of a $VOPO_4 \cdot 2H_2O$ catalyst obtained in synthesizing a VPO catalyst having a single phase according to Example 1 of the present invention.

Unless defined otherwise, all technical and scientific terms used herein have the same meanings commonly understood by those skilled in the art to which the present invention pertains. In general, the nomenclature used herein is well known in the art and is commonly used.

The present invention recognizes that nitrous oxide produced as a by-product in the existing adipic acid and dodecanedioic acid production processes is a greenhouse gas and adversely affects the environment, and finds that adipic acid and dodecanedioic acid may be produced from cyclohexane and cyclododecane, respectively, without producing the greenhouse gas described above by using a vanadium phosphorus oxide (VPO) or cobalt-manganese oxide catalyst supported on a mesoporous silica support. In addition, it was found that when cyclohexanone and cyclododecanone were additionally added to the oxidation reaction of cyclohexane and cyclododecane used as reactants, the yields of the respective products, adipic acid and dodecanedioic acid, increased.

Accordingly, the present invention relates to a method for preparing hydrocarbon double acids, the method including oxidizing one or more cyclic hydrocarbon compounds selected from the group consisting of C6 to C12 cycloalkanes and C6 to C12 cycloketones in the presence of a vanadium phosphate oxide-based catalyst, a cobalt-manganese oxide-based catalyst, or a mixture thereof.

Herein, the C6 to C12 cycloalkane means a cyclic hydrocarbon in which 6 to 12 carbon atoms are bonded like a ring and hydrogen is bonded to each carbon atom, and examples thereof include cyclohexane ($C_6H_{12}$), cycloheptane ($C_7H_{14}$), cyclooctane ($C_8H_{16}$), cyclononane ($C_9H_{18}$), and cyclodecane ($C_{10}H_{20}$).

Herein, the C6 to C12 cycloketone means a cyclic hydrocarbon having a ketone group, 6 to 12 carbon atoms bonded like a ring, and hydrogen bonded to each carbon atom, and examples thereof include cyclohexanone ($C_6H_{10}O$) of Chemical Formula 1, cycloheptanone ($C_7H_{12}O$) of Chemical Formula 2, cyclooctanone ($C_8H_{14}O$) of Chemical Formula 3, cyclononanone ($C_9H_{16}O$) of Chemical Formula 4, and cyclododecanone ($C_{10}H_{28}O$) of Chemical Formula 5.

[Chemical Formula 1]

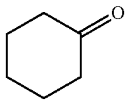

[Chemical Formula 2]

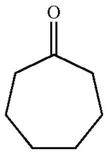

[Chemical Formula 3]

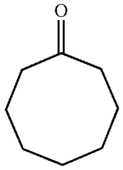

[Chemical Formula 4]

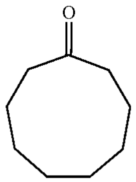

[Chemical Formula 5]

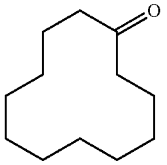

In the present invention, the cycloalkane may be cyclohexane or the cycloketone may be cyclohexanone, and in this case, the hydrocarbon double acid may be adipic acid (Chemical Formula 6).

[Chemical Formula 6]

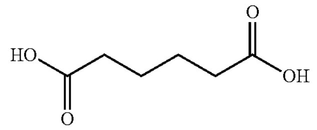

In the present invention, the cycloalkane may be cyclododecane or the cycloketone may be cyclododecanone, and in this case, the hydrocarbon hydrocarbon double acid may be dodecanedioic acid (Chemical Formula 7).

[Chemical Formula 7]

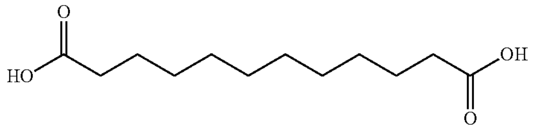

In the present invention, the cycloalkanes may be cyclohexane and cyclododecane or the cycloketones may be cyclohexanone and cyclododecanone, and in this case, the hydrocarbon double acids may be adipic acid and dodecanedioic acid.

In a preferred embodiment of the present invention, the method may include: (a) oxidizing a mixture of cyclohexane and cyclohexanone in the presence of a vanadium phosphate oxide-based catalyst, a cobalt-manganese oxide-based catalyst, or a mixture thereof to obtain adipic acid; and (b) oxidizing a mixture of cyclododecane and cyclododecanone in the presence of a vanadium phosphate oxide-based catalyst, a cobalt-manganese oxide-based catalyst, or a mixture thereof to obtain dodecanedioic acid.

In another preferred embodiment of the present invention, the method may include: (a) preparing two types of VPO-based cyclic alkane oxidation catalysts by supporting two types of VPO having a single phase on a mesoporous silica support and a cobalt-manganese oxide-based cyclic alkane oxidation catalyst by supporting a cobalt-manganese oxide precursor on a mesoporous silica support; (b) preparing linear double acids from various mixtures of cyclic alkanes and ketones using the two types of VPO-based catalysts and the cobalt-manganese oxide-based catalyst obtained in the step (a); and (c) obtaining an optimal ratio of the mixture of the two cyclic reactants in the VPO-based catalysts and the cobalt-manganese oxide-based catalyst and an optimal reaction pressure condition to maximize the yield of the linear double acids.

In the present invention, it is preferable to use the vanadium phosphate oxide-based catalyst or the cobalt-manganese oxide-based catalyst supported on a mesoporous silica support.

In the present invention, the vanadium phosphate oxide-based catalyst may be $VOPO_4 \cdot 2H_2O$, $(VO)_2P_2O_7$ or a mixture of $VOPO_4 \cdot 2H_2O$ and $(VO)_2P_2O_7$.

In the present invention, a molar ratio of manganese to cobalt in the cobalt-manganese oxide-based catalyst may be 2:0.5 to 2:4.

In the present invention, the vanadium phosphate oxide-based catalyst, the cobalt-manganese oxide-based catalyst, or the mixture thereof may be injected at a mass ratio of 0.02 to 2% with respect to the mass of the cyclic hydrocarbon compounds.

In the present invention, the oxidation may be performed at a pressure of 10 to 40 bar and a temperature of 120 to 250° C. in an oxygen atmosphere for 2 to 15 hours.

In the present invention, a content of the cyclohexanone in the mixture of cyclohexane and cyclohexanone may be 5 to 150% (molar ratio) of cyclohexane.

In the present invention, a content of the cyclododecanone in the mixture of cyclododecane and cyclododecanone may be 10 to 300% (molar ratio) of cyclododecane.

Hereinafter, the present invention will be described in detail.

A method for preparing adipic acid and dodecanedioic acid according to the present invention may include the following:

(a) preparing two types of VPO-based cyclic alkane oxidation catalysts by supporting two types of VPO having a single phase on a mesoporous silica support and a cobalt-manganese oxide-based cyclic alkane oxidation catalyst by supporting a cobalt-manganese oxide precursor on a mesoporous silica support;

(b) obtaining adipic acid from various cyclohexane-cyclohexanone mixtures using the two types of VPO-based catalysts and the cobalt-manganese oxide-based catalyst obtained in the step (a), and obtaining an optimal ratio of the two catalysts and the two reactants and an optimal reaction pressure condition in the case of the VPO-based catalyst and an optimal ratio of the two reactants and an optimal reaction pressure condition in the case of the cobalt-manganese oxide-based catalyst; and (c) obtaining dodecanedioic acid from various cyclododecane-cyclododecanone mixtures using the two types of VPO-based catalysts or the cobalt-manganese oxide-based catalyst obtained in the step (a), and obtaining an optimal ratio of the two catalysts and the two reactants and an optimal reaction pressure condition in the case of the VPO-based catalyst and an optimal ratio of the two reactants and an optimal reaction pressure condition in the case of the cobalt-manganese oxide-based catalyst.

The method for preparing adipic acid and dodecanedioic acid according to the present invention may include the following.

(a) Catalyst Synthesis Step

A method for preparing an oxidation catalyst according to the present invention includes synthesizing two types of VPO precursors having a single phase and supporting the two types of VPO precursors on mesoporous silica supports.

The method for preparing an oxidation catalyst according to the present invention includes synthesizing a cobalt-manganese oxide precursor and supporting the cobalt-manganese oxide precursor on a mesoporous silica support.

(b) Adipic Acid Preparation Step

A method for preparing adipic acid according to the present invention includes oxidizing a cyclohexane-cyclohexanone mixture in the presence of the VPO-based catalyst or the cobalt-manganese oxide-based catalyst obtained in the step (a) to obtain adipic acid.

In the method for preparing adipic acid according to the present invention, a cyclohexane-cyclohexanone mixture may be oxidized to adipic acid in an oxygen atmosphere using the VPO-based catalyst or the cobalt-manganese oxide-based catalyst.

In the cyclohexane-cyclohexanone mixture, cyclohexanone may be contained at a molar ratio of 5 to 150% with respect to cyclohexane, and preferably may be contained at a molar ratio of 25 to 50% with respect to cyclohexane. Since both cyclohexane and cyclohexanone participate in the production reaction of adipic acid, when the amount of cyclohexanone is less than 5% or more than 150% with respect to the moles of cyclohexane, adipic acid is not produced.

In the present invention, the VPO catalyst used for the oxidation reaction of the cyclohexane-cyclohexanone mixture may have a $VOPO_4 \cdot 2H_2O$ phase or $(VO)_2P_2O_7$ phase. In this case, each phase may have a mass ratio of 0 to 100% with respect to the total amount of catalysts. Therefore, only a catalyst having a $VOPO_4 \cdot 2H_2O$ phase or, conversely, only a catalyst having a $(VO)_2P_2O_7$ phase may be used, but preferably a $VOPO_4 \cdot 2H_2O$ phase may be contained at a mass ratio of 20 to 80%.

In the present invention, the cobalt-manganese oxide catalyst used in the oxidation reaction of the cyclohexane-cyclohexanone mixture may have a molar ratio of manganese to cobalt of 2:0.5 to 2:4, and preferably may have a molar ratio of manganese to cobalt of 2:2 to 2:3.

In the oxidation reaction, oxygen is used as an oxidizing agent, and the oxidation reaction may be performed at an absolute pressure of 10 to 40 bar, preferably 10 to 20 bar, and more preferably 13 to 15 bar. When the reaction is performed at a pressure of less than 10 bar, the adipic acid yield decreases due to an insufficient amount of oxidizing agent, and on the other hand, when the pressure exceeds 40 bar, the production of unwanted by-products increases, and the adipic acid yield also decreases.

In the oxidation reaction, the catalyst may be added at a mass ratio of 0.02 to 2% with respect to the mass of cyclohexane and cyclohexanone, which are reactants. When a catalyst having a mass ratio of less than 0.02% is used, the reactants are not sufficiently oxidized due to a relatively insufficient amount of catalyst, and when the mass ratio exceeds 2%, it is economically insufficient because the adipic acid conversion does not increase compared to the increased amount of catalyst.

In the oxidation reaction, the temperature of the reactant may be 120 to 250° C., preferably 120 to 160° C., and more preferably 135 to 145° C. When the temperature of the reactant is lower than 120° C., adipic acid is not produced, and conversely, when the temperature of the reactant is higher than 250° C., a reaction in which produced adipic acid is decomposed may occur.

The oxidation reaction may proceed for a reaction time of 2 to 15 hours after the temperature rises.

In the oxidation reaction, the cyclohexane-cyclohexanone conversion or the adipic acid yield may vary depending on the temperature of the reactant, the oxygen pressure, the amount of catalyst, and the relative ratio of cyclohexane and cyclohexanone.

(c) Dodecanedioic Acid Preparation Step

A method for preparing dodecanedioic acid according to the present invention includes oxidizing a cyclododecane-cyclododecanone mixture in the presence of the VPO-based catalyst or the cobalt-manganese oxide-based catalyst obtained in the step (a) to obtain dodecanedioic acid.

In the method for preparing dodecanedioic acid according to the present invention, a cyclododecane-cyclododecanone mixture may be oxidized to dodecanedioic acid in an oxygen atmosphere using the VPO-based catalyst or the cobalt-manganese oxide-based catalyst.

In the cyclododecane-cyclododecanone mixture, cyclododecanone may be contained at a molar ratio of 10 to 300% with respect to cyclododecane, and preferably may be contained at a molar ratio of 25 to 50% with respect to cyclododecane.

In the present invention, the VPO catalyst used for the oxidation reaction of the cyclododecane-cyclododecanone mixture may have a $VOPO_4 \cdot 2H_2O$ phase or $(VO)_2P_2O_7$ phase. In this case, each phase may have a mass ratio of 0 to 100% with respect to the total amount of catalysts. Therefore, only a catalyst having a $VOPO_4 \cdot 2H_2O$ phase or, conversely, only a catalyst having a $(VO)_2P_2O_7$ phase may be used, but preferably a $VOPO_4 \cdot 2H_2O$ phase may be contained at a mass ratio of 20 to 80%.

In the present invention, the cobalt-manganese oxide catalyst used in the oxidation reaction of the cyclododecane-cyclododecanone mixture may have a molar ratio of manganese to cobalt of 2:0.5 to 2:4, and preferably may have a molar ratio of manganese to cobalt of 2:2 to 2:3.

In the oxidation reaction, oxygen is used as an oxidizing agent, and the oxidation reaction may be performed at an absolute pressure of 10 to 20 bar and preferably 13 to bar. When the reaction is performed at a pressure of less than 10 bar, the dodecanedioic acid yield decreases due to an insufficient amount of oxidizing agent, and on the other hand, when the pressure exceeds 20 bar, the production of unwanted by-products increases, and the dodecanedioic acid yield also decreases.

In the oxidation reaction, the catalyst may be added at a mass ratio of 0.02 to 2% with respect to the mass of cyclododecane and cyclododecanone, which are reactants. When a catalyst having a mass ratio of less than 0.02% is used, the reactants are not sufficiently oxidized due to a relatively insufficient amount of catalyst, and when the mass ratio exceeds 2%, it is economically insufficient because the dodecanedioic acid conversion does not increase compared to the increased amount of catalyst.

In the oxidation reaction, the temperature of the reactant may be 120 to 160° C. and preferably 135 to 145° C. When the temperature of the reactant is lower than 120° C., dodecanedioic acid is not produced, and conversely, when the temperature of the reactant is higher than 160° C., a reaction in which produced dodecanedioic acid is decomposed may occur.

The oxidation reaction may proceed for a reaction time of 2 to 15 hours after the temperature rises.

In the oxidation reaction, the cyclododecane-cyclododecanone conversion or the dodecanedioic acid yield may vary depending on the temperature of the reactant, the oxygen pressure, the amount of catalyst, and the relative ratio of cyclododecane and cyclododecanone.

Hereinafter, preferred Examples will be provided in order to assist in the understanding of the present invention. However, it will be obvious to those skilled in the art that the following Examples are only examples of the present invention and various modifications and alterations may be made without departing from the scope and spirit of the present invention. In addition, these modifications and alterations will fall within the appended claims.

EXAMPLES

Example 1: Preparation of VPO Catalyst Supported on Mesoporous Silica Support Two types of VPO precursors having a single phase were synthesized and supported on mesoporous silica supports having a high surface area, respectively.

6 g of vanadium (V) oxide ($V_2O_5$, ≥99.6%, Sigma-Aldrich), 8.3 g of phosphoric acid ($H_3PO_4$, min. 89.0 w/w %, TCI), and 125 mL of isobutanol (>99%, TCI) were put into a 250 mL round-bottomed flask, and reflux was performed at 100° C. for 16 hours. Thereafter, the solution was filtered through a 0.8 μm filter paper, and 100 mL of acetone (>99.5%, TCI) was put into a 250 ml beaker, and then stirring was performed at 300 rpm for 30 minutes for washing. Thereafter, the washing-filtration process described above was repeated three times in total, and drying was performed at 90° C. for 12 hours.

The dried solid put into an alumina crucible was placed in a reactor, and then a firing process was performed in a state in which both ends of the crucible were opened to allow air to flow in and out. At this time, the temperature of the reactor was raised from 20° C. to 550° C. at a rate of 5° C./min, maintained at 550° C. for 3 hours, and then cooled to room temperature, thereby obtaining a $VOPO_4 \cdot 2H_2O$ catalyst.

In the above process, the dried solid put into an alumina crucible was placed in a reactor, and then a firing process was performed while allowing helium (He, >99.999%, SAMO SPECIALITY GAS CO., LTD.) to flow at a flow rate of 50 mL/min. At this time, the temperature of the reactor was raised from 20° C. to 550° C. at a rate of 5° C./min, maintained at 550° C. for 3 hours, and then cooled to room temperature, thereby obtaining a $(VO)_2P_2O_7$ catalyst.

In the above process, the solid and mesoporous silica (MCM-41, 4.5 to 4.8 nm, Sigma-Aldrich) were put into a 250 mL beaker so that the content of the dried solid was 5 wt %, 30 mL of distilled water per 1 g of the solid was added, and then stirring was performed at room temperature for 24 hours.

Thereafter, the solid remaining after evaporating all distilled water was dried at 100° C. The solid put into an alumina crucible was placed in a reactor, and then a firing process was performed in a state in which both ends of the crucible were opened to allow air to flow in and out. At this time, the temperature of the reactor was raised from 20° C. to 550° C. at a rate of 5° C./min, maintained at 550° C. for 3 hours, and then cooled to room temperature, thereby obtaining a $VOPO_4 \cdot 2H_2O$ catalyst supported on a mesoporous silica support. In addition, the dried solid subjected to the drying process put into an alumina crucible was placed in a reactor, and then a firing process was performed while allowing helium (He, >99.999%, SAMO SPECIALITY GAS CO., LTD.) to flow at a flow rate of 50 mL/min. At this time, the temperature of the reactor was raised from 20° C. to 550° C. at a rate of 5° C./min, maintained at 550° C. for 3 hours, and then cooled to room temperature, thereby obtaining a $(VO)_2P_2O_7$ catalyst supported on a mesoporous silica support.

Figure 2:
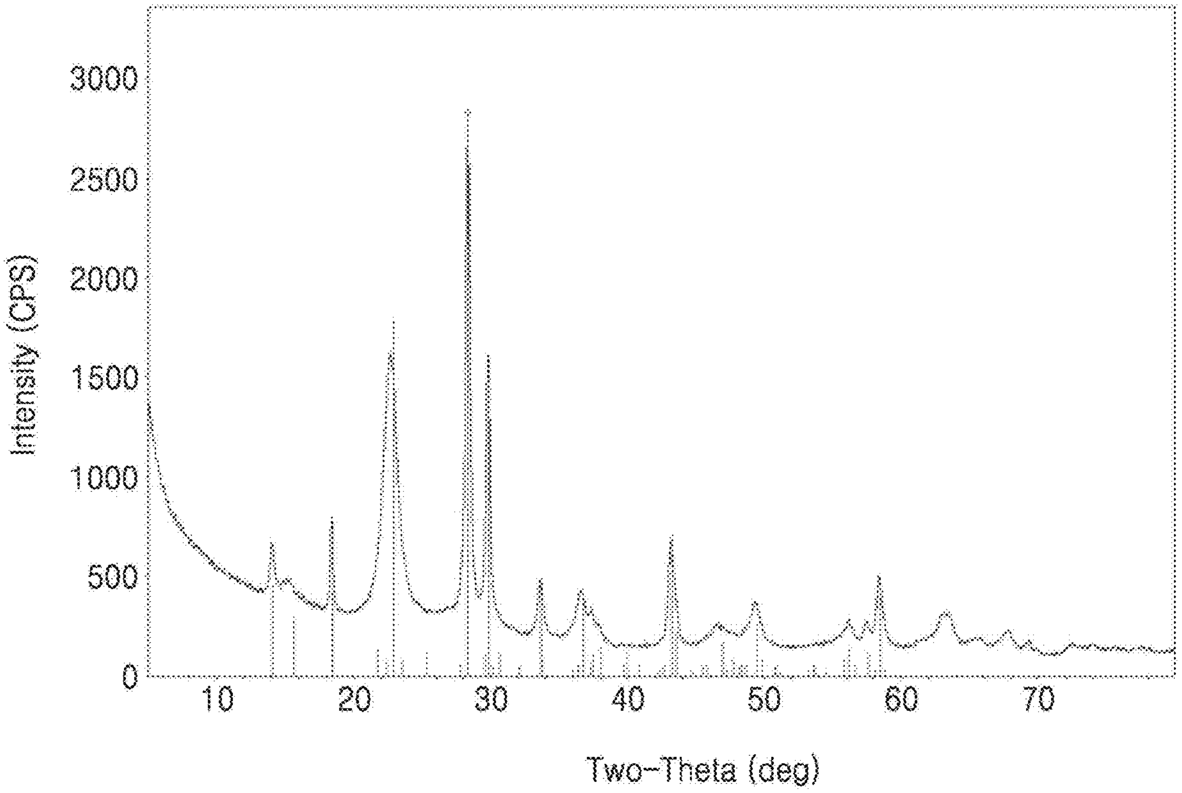
FIG. 2 is a graph showing a schematic form of XRD peaks of a $(VO)_2P_2O_7$ catalyst obtained in synthesizing the VPO catalyst having a single phase according to Example 1 of the present invention.

The synthesized catalyst was analyzed through XRD (Smartlab). The schematic form of XRD peaks of the synthesized $VOPO_4 \cdot 2H_2O$ catalyst and the schematic form of XRD peaks of the $(VO)_2P_2O_7$ catalyst are illustrated in FIGS. 1 and 2, respectively.

Example 2: Preparation of Cobalt-Manganese Oxide Catalyst Supported on Mesoporous Silica Support A cobalt-manganese oxide precursor was synthesized, and the synthesized cobalt-manganese oxide precursor was supported on a mesoporous silica support having a high surface area.

$Co(NO_3)_2 \cdot 6H_2O$ and $Mn(NO_3)_2$ were put into a 250 ml beaker so that a molar ratio of manganese to cobalt was 2:3, and then distilled water was added until all solids were completely dissolved. The temperature of the solution was raised to 60° C. using a hot plate, and stirring was performed at a rate of 300 rpm. Thereafter, while a pH of the solution was measured using a pH meter, 1 mol/L of a sodium hydroxide aqueous solution was added dropwise into the solution using a burette until the pH reached 8. Aging was performed by continuously stirring the solution for 4 hours while maintaining the temperature of the solution at 60° C., and the resulting solution was filtered through a 0.8 μm filter paper. Thereafter, 100 mL of distilled water was put into a 250 mL beaker, and stirring was performed at room temperature and 300 rpm for 30 minutes for washing. Thereafter, the washing-filtration process described above was repeated three times in total, and drying was performed at 120° C. for 12 hours.

The solid and mesoporous silica (MCM-41, 4.5 to 4.8 nm, Sigma-Aldrich) were put into a 250 ml beaker so that the content of the dried solid was 5 wt %, 30 mL of distilled water per 1 g of the solid was added, and then stirring was performed at room temperature for 24 hours. Thereafter, the solid remaining after evaporating all distilled water was dried at 100° C. The dried solid put into an alumina crucible was placed in a reactor, and then a firing process was performed in a state in which both ends of the crucible were opened to allow air to flow in and out. At this time, the temperature of the reactor was raised from 20° C. to 400° C. at a rate of 5° C./min, maintained at 400° C. for 4 hours, and then cooled to room temperature, thereby obtaining a cobalt-manganese oxide catalyst supported on a mesoporous silica support.

Figure 3:
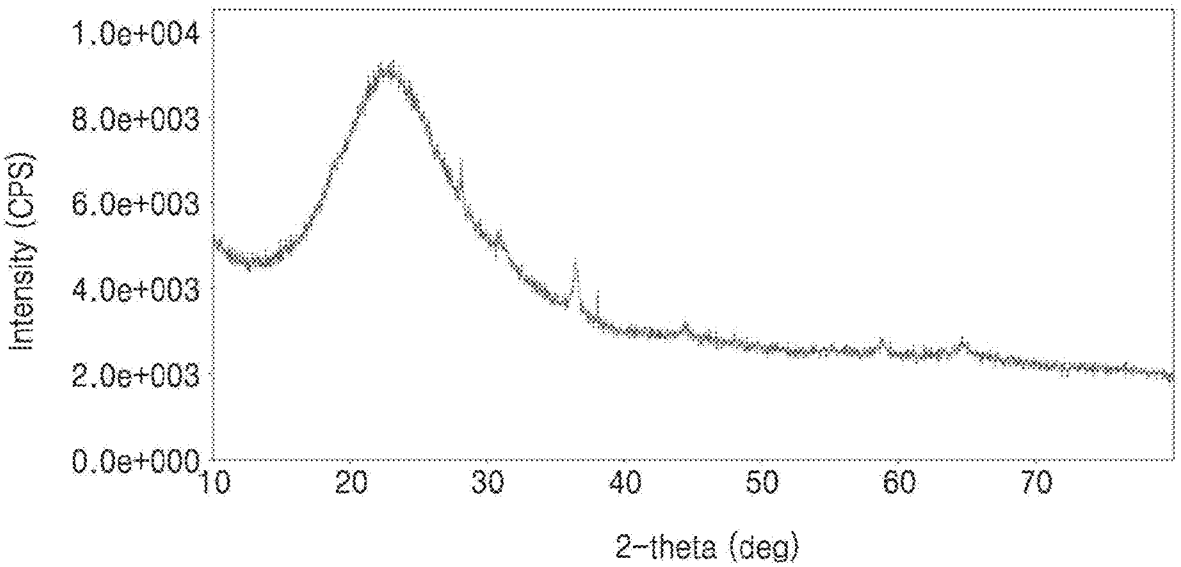
FIG. 3 is a graph showing a schematic form of XRD peaks of a cobalt-manganese oxide catalyst obtained according to Example 2 of the present invention.

The synthesized catalyst was analyzed through XRD (Smartlab). The schematic form of XRD peaks of the synthesized cobalt-manganese oxide catalyst are illustrated in FIG. 3.

Example 3: Determination of Optimal Ratio of VPO Catalysts Having Two Types of Phases and Optimal Ratio of Cyclohexane-Cyclohexanone Mixture in Adipic Acid Production Reaction An optimal value in the reaction in which a cyclohexane-cyclohexanone mixture was converted to adipic acid in the presence of the corresponding catalyst was determined while changing the relative amounts of two VPO catalysts having a single phase and the ratio of the cyclohexane-cyclohexanone mixture.

mL of cyclohexane, and cyclohexanone corresponding to each of 0, 25, 50, 100, 150, and 200% with respect to the moles of cyclohexane, respectively, were injected into the reactor. Thereafter, while maintaining the total amount of the catalysts at 15 mg, a reaction experiment was conducted while increasing the mass ratios of the VPO catalysts having a $VOPO_4 \cdot 2H_2O$ phase to 0, 50, 80, and 100%, respectively. The temperature of the reactant was raised to 135° C., and when the temperature reached a set value, the reactor was charged with 13 bar of oxygen, and then the reactant was oxidized for 5 hours.

The product after the reaction was quantitatively analyzed through On-line GC (Agilent 7890A). Tables 1 to 4 show the cyclohexane conversion and the adipic acid yield when the mass ratios of the VPO catalysts having a $VOPO_4 \cdot 2H_2O$ phase, confirmed through the quantitative analysis, were 0, 50, 80, and 100%, respectively.

The adipic acid yield was higher when the $(VO)_2P_2O_7$/MCM-41 catalyst was used than when the $VOPO_4 \cdot 2H_2O$/MCM-41 catalyst was used. In addition, the adipic acid yield increased when two catalysts were used together than when only a single phase was used as a catalyst. In a case where the ratio of the two catalysts was 1:1, when a molar ratio of cyclohexane to cyclohexanone was 1:0.25, the adipic acid yield was the highest, and in a case where a ratio of the $VOPO_4 \cdot 2H_2O$/MCM-41 catalyst accounted for 80% of the total mass of the catalysts, when a molar ratio of cyclohexane to cyclohexanone was 1:0.5, adipic acid was produced the most.

In addition, when only cyclohexane was present or when the ratio of cyclohexanone was too high, adipic acid was not produced. This means that when the current catalyst system is used, the reaction proceeds to adipic acid only when cyclohexanone is present. In addition, it was confirmed that adipic acid was not always produced simply by the presence of cyclohexanone, and adipic acid could be obtained only when cyclohexane and cyclohexanone were present at an appropriate ratio.

Example 4: Effect of Oxygen Pressure in Adipic Acid Production Reaction Using VPO Catalyst Supported on Mesoporous Silica The effect of increasing the oxygen pressure on the production of adipic acid in the oxidation reaction of the cyclohexane-cyclohexanone mixture using both the two VPO catalysts having a single phase was confirmed.

10 mL of cyclohexane and cyclohexanone corresponding to 50% of the moles of cyclohexane were injected into the reactor. Thereafter, while maintaining the total amount of the catalysts at 15 mg, a reaction experiment was conducted by setting the mass ratios of the VPO catalysts having a $VOPO_4 \cdot 2H_2O$ phase to 50 and 80%, respectively. The temperature of the reactant was raised to 135° C., and when the temperature reached a set value, the reactor was charged with 13, 15, or 17 bar of oxygen, and then the reactant was oxidized for 5 hours.

The product after the reaction was quantitatively analyzed through On-line GC (Agilent 7890A). Tables 5 and 6 show the cyclohexane conversion and the adipic acid yield at various oxygen pressures (13 to 17 bar) when the mass ratios of the VPO catalysts having a $VOPO_4 \cdot 2H_2O$ phase, confirmed through the quantitative analysis, were 50 and 80%, respectively.

When the oxygen pressure was increased from 13 bar to bar, the adipic acid yield increased. This shows that the supply of oxygen is significantly important in the production of adipic acid. However, when the oxygen pressure was additionally increased to 17 bar, the adipic acid selectivity decreased and the overall adipic acid yield decreased. Accordingly, it was confirmed that unwanted side reactions occur when the amount of oxygen supplied exceeds a certain level.

Example 5: Effect of Oxygen Pressure in Adipic Acid Production Reaction Using Cobalt-manganese Oxide Catalyst Supported on Mesoporous Silica The effect of increasing the oxygen pressure on the production of adipic acid in the oxidation reaction of the cyclohexane-cyclohexanone mixture using the cobalt-manganese oxide catalyst supported on mesoporous silica was confirmed.

10 mL of cyclohexane and cyclohexanone corresponding to 50% of the moles of cyclohexane were injected into the reactor. Thereafter, 15 mg of the cobalt-manganese oxide catalyst was injected, and the temperature of the reactant was raised to 135° C. When the temperature reached a set value, the reactor was charged with 13, 15, or 17 bar of oxygen, and then the reactant was oxidized for 5 hours.

The product after the reaction was quantitatively analyzed through On-line GC (Agilent 7890A). Table 7 shows the effect of various oxygen pressures (13 to 17 bar) on the cyclohexane conversion and the adipic acid yield in the presence of the cobalt-manganese oxide catalyst supported on a mesoporous silica support confirmed through the quantitative analysis.

Even in a case where the cobalt-manganese oxide catalyst was used, when the oxygen pressure was increased from 13 bar to 15 bar, the adipic acid yield increased as in the case of using the VPO catalyst described above, and when the oxygen pressure was increased to 17 bar, the adipic acid selectivity decreased and the overall adipic acid yield decreased.

Example 6: Determination of Optimal Ratio of VPO Catalysts Having Two Types of Phases and Supported on Mesoporous Silica Support in Production Reaction of Dodecanedioic Acid While changing the relative amount of the two VPO catalysts supported on mesoporous silica supports and having a single phase, an optimal value in the reaction in which the cyclododecane-cyclododecanone mixture was converted to dodecanedioic acid in the presence of the corresponding catalyst was determined.

The sum of the number of moles of cyclododecane and cyclododecanone was set to 92.45 mmol, a molar ratio of cyclododecane was set to 25%, a molar ratio of cyclododecanone was set to 75%, and the two materials were injected into the reactor. Thereafter, while maintaining the total amount of the catalysts at 15 mg, a reaction experiment was conducted while increasing the mass ratios of the VPO catalysts having a $VOPO_4 \cdot 2H_2O$ phase to 0, 50, and 100%, respectively. The temperature of the reactant was raised to 135° C., and when the temperature reached a set value, the reactor was charged with 13 bar of oxygen, and then the reactant was oxidized for 5 hours.

The product after the reaction was quantitatively analyzed through NMR. At this time, 1 mL of chloroform-D and 20 μL of dimethyl sulfoxide-D6 were used together as a solvent, and 0.01 mmol of ethylene carbonate was used as a standard solution. Table 8 shows the effect of the various mass ratios of $VOPO_4 \cdot 2H_2O$ phases on the dodecanedioic acid yield in the presence of the VPO catalyst supported on a mesoporous silica support confirmed through NMR.

The dodecanedioic acid yield was higher when the $(VO)_2P_2O_7$/MCM-41 catalyst was used than when the $VOPO_4 \cdot 2H_2O$/MCM-41 catalyst was used. Unlike the case of using only a single phase as a catalyst, the dodecanedioic acid yield when the two catalysts were mixed at mass ratios of 50%, respectively, was almost the same as when the $VOPO_4 \cdot 2H_2O$/MCM-41 catalyst was used.

Example 7: Determination of Optimal Ratio of Cyclododecane-Cyclododecanone Mixture in Dodecanedioic Acid Production Reaction Using Cobalt-manganese Oxide Supported on Mesoporous Silica While changing the ratio of the cyclododecane-cyclododecanone mixture in the oxidation reaction of the cyclododecane-cyclododecanone mixture using the cobalt-manganese oxide catalyst supported on a mesoporous silica support, an optimal ratio value in the reaction in which the was converted to cyclododecane-cyclododecanone mixture dodecanedioic acid in the presence of the corresponding catalyst was determined.

The sum of the number of moles of the cyclododecane and cyclododecanone was set to 92.45 mmol, and the ratio of the mixture was changed while increasing the molar ratio of cyclododecanone to 0, 25, 50, 75, and 100%. 15 mg of the cobalt-manganese oxide catalyst was injected together with the corresponding mixture, and the temperature of the reactant was raised to 135° C. When the temperature reached a set value, the reactor was charged with 13 bar of oxygen, and then the reactant was oxidized for 5 hours.

The product after the reaction was quantitatively analyzed through NMR. At this time, 1 mL of chloroform-D and 20 μL of dimethyl sulfoxide-D6 were used together as a solvent, and 0.01 mmol of ethylene carbonate was used as a standard solution. Table 9 shows the effect of various ratios of the cyclododecane-cyclododecanone mixtures on the dodecanedioic acid yield in the presence of the cobalt-manganese oxide catalyst supported on a mesoporous silica support confirmed through NMR.

Dodecanedioic acid was formed even when each of cyclododecane and cyclododecanone was used alone, but the dodecanedioic acid yield increased when a mixture of cyclododecane and cyclododecanone was used. Through this, it was confirmed that in the reaction in which cyclododecane was converted to dodecanedioic acid, cyclododecanone, an intermediate material of the reaction, was additionally added, such that the induction time was reduced, and thus the production of dodecanedioic acid was accelerated.

TABLE 1

Cyclohexane conversion and adipic acid yield when mass ratio of VPO catalyst having $VOPO_4 \cdot 2H_2O$ phase is 0%

| | Cyclohexane:cyclohexanone ratio | | | | | |
|---|---|---|---|---|---|---|
| | 1:0 | 1:0.25 | 1:0.5 | 1:1 | 1:1.5 | 1:2 |
| Cyclohexane conversion (%) | 13.63 | 32.49 | 28.91 | 19.28 | 19.12 | 18.03 |
| Adipic acid selectivity (%) | 0 | 23.77 | 21.61 | 27.38 | 0 | 0 |
| Adipic acid yield (%) | 0 | 7.72 | 6.25 | 5.28 | 0 | 0 |

TABLE 2

Cyclohexane conversion and adipic acid yield when mass ratio of VPO catalyst having $VOPO_4 \cdot 2H_2O$ phase is 50%

| | Cyclohexane:cyclohexanone | | | | | |
|---|---|---|---|---|---|---|
| | 1:0 | 1:0.25 | 1:0.5 | 1:1 | 1:1.5 | 1:2 |
| Cyclohexane conversion (%) | 19.69 | 44.84 | 41.36 | 20.91 | 12.34 | 49.72 |
| Adipic acid selectivity (%) | 0 | 21.20 | 19.49 | 24.71 | 38.79 | 0 |
| Adipic acid yield (%) | 0 | 9.51 | 8.06 | 5.17 | 4.79 | 0 |

TABLE 3

Cyclohexane conversion and adipic acid yield when mass ratio of VPO catalyst having $VOPO_4 \cdot 2H_2O$ phase is 80%

| | Cyclohexane:cyclohexanone | | | | | |
|---|---|---|---|---|---|---|
| | 1:0 | 1:0.25 | 1:0.5 | 1:1 | 1:1.5 | 1:2 |
| Cyclohexane conversion (%) | 25.73 | 46.77 | 28.90 | 11.09 | 21.40 | 24.88 |
| Adipic acid selectivity (%) | 0 | 14.22 | 32.89 | 48.43 | 14.97 | 0 |
| Adipic acid yield (%) | 0 | 6.65 | 9.51 | 5.37 | 3.20 | 0 |

TABLE 4

Cyclohexane conversion and adipic acid yield when mass ratio of VPO catalyst having $VOPO_4 \cdot 2H_2O$ phase is 100%

| | Cyclohexane:cyclohexanone | | | | | |
|---|---|---|---|---|---|---|
| | 1:0 | 1:0.25 | 1:0.5 | 1:1 | 1:1.5 | 1:2 |
| Cyclohexane conversion (%) | 20.53 | 31.29 | 27.21 | 19.99 | 24.74 | 20.93 |
| Adipic acid selectivity (%) | 0 | 16.69 | 20.63 | 0 | 0 | 0 |
| Adipic acid yield (%) | 0 | 5.22 | 5.61 | 0 | 0 | 0 |

TABLE 5

Effect of various oxygen pressures (13 to 17 bar) on cyclohexane conversion and adipic acid yield in presence of catalyst having mass ratio of $VOPO_4 \cdot 2H_2O$ of 50% and supported on mesoporous silica support

| | Cyclohexane: cyclohexanone = 1:0.5 13 bar, 135° C. | Cyclohexane: cyclohexanone = 1:0.5 15 bar, 135° C. | Cyclohexane: cyclohexanone = 1:0.5 17 bar, 135° C. |
|---|---|---|---|
| Cyclohexane conversion (%) | 41.36 | 26.61 | 44.80 |
| Adipic acid selectivity (%) | 19.49 | 41.53 | 22.23 |
| Adipic acid yield (%) | 8.06 | 11.05 | 9.96 |

TABLE 6

Effect of various oxygen pressures (13 to 17 bar) on cyclohexane conversion and adipic acid yield in presence of catalyst having mass ratio of $VOPO_4 \cdot 2H_2O$ of 80% and supported on mesoporous silica support

| | Cyclohexane: cyclohexanone = 1:0.5 13 bar, 135° C. | Cyclohexane: cyclohexanone = 1:0.5 15 bar, 135° C. | Cyclohexane: cyclohexanone = 1:0.5 17 bar, 135° C. |
|---|---|---|---|
| Cyclohexane conversion (%) | 28.90 | 33.80 | 35.11 |
| Adipic acid selectivity (%) | 32.89 | 30.29 | 25.48 |
| Adipic acid yield (%) | 9.51 | 10.24 | 8.94 |

TABLE 7

Effect of various oxygen pressures (13 to 17 bar) on cyclohexane conversion and adipic acid yield in presence of cobalt-manganese oxide catalyst

| | Cyclohexane: cyclohexanone = 1:0.5 13 bar, 135° C. | Cyclohexane: cyclohexanone = 1:0.5 15 bar, 135° C. | Cyclohexane: cyclohexanone = 1:0.5 17 bar, 135° C. |
|---|---|---|---|
| Cyclohexane conversion (%) | 29.04 | 22.17 | 16.17 |
| Adipic acid selectivity (%) | 43.58 | 57.08 | 60.55 |
| Adipic acid yield (%) | 12.66 | 12.66 | 9.79 |

TABLE 8

Effect of various mass ratios of $VOPO_4 \cdot 2H_2O$ phases on dodecanedioic acid yield in presence of VPO catalyst supported on mesoporous silica support

| | $(VO)_2P_2O_7$: $VOPO_4 \cdot 2H_2O$ = 1:0 13 bar, 135° C. | $(VO)_2P_2O_7$: $VOPO_4 \cdot 2H_2O$ = 0.5:0.5 13 bar, 135° C. | $(VO)_2P_2O_7$: $VOPO_4 \cdot 2H_2O$ = 0:1 13 bar, 135° C. |
|---|---|---|---|
| Cyclododecane conversion (%) | 37.54 | 30.36 | 57.34 |
| Dodecanedioic acid selectivity (%) | 55.44 | 66.92 | 30.53 |
| Dodecanedioic acid yield (%) | 20.82 | 20.32 | 17.51 |

TABLE 9

Effect of various ratios of cyclododecane-cyclododecanone mixtures on dodecanedioic acid yield in presence of cobalt-manganese oxide catalyst supported on mesoporous silica support

| | Cyclododecane: cyclododecanone = 100:0 13 bar, 135° C. | Cyclododecane: cyclododecanone = 75:25 13 bar, 135° C. | Cyclododecane: cyclododecanone = 50:50 13 bar, 135° C. |
|---|---|---|---|
| Cyclododecane conversion (%) | 10.84 | 54.52 | 48.72 |
| Dodecanedioic acid selectivity (%) | 51.92 | 42.59 | 47.91 |
| Dodecanedioic acid yield (%) | 5.63 | 23.22 | 23.35 |

TABLE 9-continued

Effect of various ratios of cyclododecane-cyclododecanone mixtures on dodecanedioic acid yield in presence of cobalt-manganese oxide catalyst supported on mesoporous silica support

| | Cyclododecane: cyclododecanone = 25:75 13 bar, 135° C. | Cyclododecane: cyclododecanone = 0:100 13 bar, 135° C. |
|---|---|---|
| Cyclododecane conversion (%) | 35.19 | 28.71 |
| Dodecanedioic acid selectivity (%) | 84.82 | 70.19 |
| Dodecanedioic acid yield (%) | 29.84 | 20.15 |

According to the preparation method of the present invention, VPO or cobalt-manganese oxide supported on a mesoporous silica support is used as a catalyst, such that linear double acids such as adipic acid and dodecanedioic acid may be obtained without production of greenhouse gas nitrous oxide, which is a by-product in the existing process. Further, the cyclic ketone is added to the cyclic alkane as a reactant, such that each of the double acids may be obtained with a higher yield than when the cyclic alkane is used as a single reactant.

Special portions of contents of the present invention have been described in detail hereinabove, and it will be obvious to those skilled in the art that this detailed description is only an embodiment and the scope of the present invention is not limited by this detailed description. Therefore, the substantial scope of the present invention will be defined by the claims and equivalents thereof.

The invention claimed is:

1. A method for preparing hydrocarbon double acids, the method comprising oxidizing one or more cyclic hydrocarbon compounds selected from the group consisting of $C_6$ to $C_{12}$ cycloalkanes and $C_6$ to $C_{12}$ cycloketones in the presence of a vanadium phosphate oxide-based catalyst, a cobalt-manganese oxide-based catalyst, or a mixture thereof, wherein the cycloalkane is cyclododecane or the cycloketone is cyclododecanone, and the hydrocarbon double acid is dodecanedioic acid.

2. The method of claim 1, wherein the cycloalkanes are a mixture of cyclohexane and cyclododecane or the cycloketones are a mixture of cyclohexanone and cyclododecanone, and the hydrocarbon double acids are adipic acid and dodecanedioic acid.

3. The method of claim 1, wherein the vanadium phosphate oxide-based catalyst or the cobalt-manganese oxide-based catalyst is supported on a mesoporous silica support.

4. The method of claim 1, wherein the vanadium phosphate oxide-based catalyst is $VOPO_4 \cdot 2H_2O$, $(VO)_2P_2O_7$ or a mixture of $VOPO_4 \cdot 2H_2O$ and $(VO)_2P_2O_7$.

5. The method of claim 1, wherein a molar ratio of manganese to cobalt in the cobalt-manganese oxide-based catalyst is 2:0.5 to 2:4.

6. The method of claim 1, wherein the vanadium phosphate oxide-based catalyst, the cobalt-manganese oxide-based catalyst, or the mixture thereof is injected at a mass ratio of 0.02 to 2% with respect to the mass of the cyclic hydrocarbon compounds.

7. The method of claim 1, wherein the oxidation is performed at a pressure of 10 to 40 bar and a temperature of 120 to 250° C. in an oxygen atmosphere for 2 to 15 hours.

8. A method for preparing hydrocarbon double acids, the method comprising oxidizing one or more cyclic hydrocarbon compounds selected from the group consisting of $C_6$ to $C_{12}$ cycloalkanes and $C_6$ to $C_{12}$ cycloketones in the presence of a vanadium phosphate oxide-based catalyst, a cobalt-manganese oxide-based catalyst, or a mixture thereof, wherein the method comprises:

(a) oxidizing a mixture of cyclohexane and cyclohexanone in the presence of a vanadium phosphate oxide-based catalyst, a cobalt-manganese oxide-based catalyst, or a mixture thereof to obtain adipic acid; and (b) oxidizing a mixture of cyclododecane and cyclododecanone in the presence of a vanadium phosphate oxide-based catalyst, a cobalt-manganese oxide-based catalyst, or a mixture thereof to obtain dodecanedioic acid.

9. The method of claim 8, wherein a content of the cyclohexanone in the mixture of cyclohexane and cyclohexanone is 5 to 150% (molar ratio) of the cyclohexane.

10. The method of claim 8, wherein a content of the cyclododecanone in the mixture of cyclododecane and cyclododecanone is 10 to 300% (molar ratio) of the cyclododecane.

11. The method of claim 8, wherein the vanadium phosphate oxide-based catalyst or the cobalt-manganese oxide-based catalyst is supported on a mesoporous silica support.

12. The method of claim 8, wherein the vanadium phosphate oxide-based catalyst is $VOPO_4 \cdot 2H_2O$, $(VO)_2P_2O_7$ or a mixture of $VOPO_4 \cdot 2H_2O$ and $(VO)_2P_2O_7$.

13. The method of claim 8, wherein a molar ratio of manganese to cobalt in the cobalt-manganese oxide-based catalyst is 2:0.5 to 2:4.

14. The method of claim 8, wherein the vanadium phosphate oxide-based the cobalt-manganese oxide-based catalyst, or the mixture thereof is injected at a mass ratio of 0.02 to 2% with respect to the mass of the cyclic hydrocarbon compounds.

15. The method of claim 8, wherein the oxidation is performed at a pressure of 10 to 40 bar and a temperature of 120 to 250° C. in an oxygen atmosphere for 2 to 15 hours.

* * * * *